United States Patent
Holmes et al.

(10) Patent No.: US 7,923,584 B2
(45) Date of Patent: Apr. 12, 2011

(54) SYNTHESIS OF DIFUNCTIONAL OXYETHYLENE-BASED COMPOUNDS

(75) Inventors: Brian T Holmes, Arlington, VA (US); Arthur W Snow, Alexandria, VA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 167 days.

(21) Appl. No.: 12/358,296

(22) Filed: Jan. 23, 2009

(65) Prior Publication Data

US 2009/0187037 A1 Jul. 23, 2009

Related U.S. Application Data

(60) Provisional application No. 61/022,843, filed on Jan. 23, 2008.

(51) Int. Cl.
*C07C 43/00* (2006.01)
(52) U.S. Cl. .......................... 568/614; 558/10
(58) Field of Classification Search ................. 568/614; 558/10
See application file for complete search history.

(56) References Cited

FOREIGN PATENT DOCUMENTS

| CA | 2309684 | * | 3/2000 |
|----|---------|---|--------|
| SU | 419503  |   | 3/1974 |

OTHER PUBLICATIONS

Maksyuta et al., Russian J. Org. Chem., 2001; 37(6):814-818.*
(Dörwald, F. Zaragoza. Side Reactions in Organic Synthesis: A Guide to Successful Synthesis Design, Weinheim: WILEY-VCH Verlag GmbH & Co. KGaA, 200.*
Qu et al (J. Med. Chem. 2007, 50, 2157-2165).*
Zhang et al. (J. Med. Chem. 2005, 48, 5980-5988).*
Yu et al. (Bulletin of the Korean Chemical Society (2004), 25(4), 506-510).*
Abdel-Jalil et al. (J. Radioanal. Nucl. Chem. 2006, 267(3); 557-560).*
Kollhofer et al. (Chemistry-A European Journal, 2003, 9(6); 1416-1425).*
Holmes et al. , "Practical use of NH4X salts for difunctional oxyethylene-based intermediates" Tetrahedron Lett., 48, 4813-4815 (2007).
Mueller et al., "Nucleophilic Substitution in Dipolar Aprotic Solvents: Hexamethylphosphoric Triamide" Helvetica Chimica Acta, 55(8), 2965-2971 (1972).
Nagatsugi et al., "Synthesis of w-fluorinated octanoic acid and its b-substituted derivatives" J. Fluorine Chem., 56, 373-383 (1992).
Selve et al., "Monodisperse Perfluoro-Polyethoxylated Amphiphilic Compounds with Two-Chain Polar Head—Preparation and Properties" Tetrahedron, 47, 411-428 (1991).
Snow et al., "Conversion of Alcohols to Thiols via Tosylate Intermediates" Synthesis, 4, 509 (2003).
Tang et al., "Convergent synthesis of AB2-AB3 hybrid-type of amphiphilic oligoethyleneoxy-modified poly(benzyl ether) dendrons" J. Chem. Res., Synopses, 11, 698-699 (2003).

* cited by examiner

*Primary Examiner* — Yong Chu
*Assistant Examiner* — Valerie Rodriguez-Garcia
(74) *Attorney, Agent, or Firm* — Amy L. Ressing; Joseph T. Grunkemeyer

(57) ABSTRACT

A method of reacting a toluenesulfonyl-terminated polyoxyethylene compound having the formula $CH_3$—$C_6H_4$—$SO_2$—$(O$—$CH_2$—$CH_2)_n$—$O$—$R^1$ with an ammonium salt having the formula $NR^2{}_4X$ to form a compound having the formula $X$—$CH_2$—$CH_2$—$(O$—$CH_2$—$CH_2)_{n-1}$—$R^3$. The value n is a positive integer. X is a halogen, cyanide, cyanate, thiocyanate, or azide. $R^1$ is a terminating group. Each $R^2$ is hydrogen or an alkyl group. —$R^3$ is —O—$R^1$ or —X.

9 Claims, No Drawings

SYNTHESIS OF DIFUNCTIONAL OXYETHYLENE-BASED COMPOUNDS

This application claims the benefit of U.S. Provisional Patent Application No. 61/022,843, filed Jan. 23, 2008. This provisional application and all other publications and patent documents referenced throughout this nonprovisional application are incorporated herein by reference.

TECHNICAL FIELD

The disclosed method is generally related to synthesis of difunctional oxyethylene-based compounds.

DESCRIPTION OF RELATED ART

Numerous short-chain oxyethylene compounds with a variety of halogen and pseudohalogen terminal functional groups have been synthesized from corresponding precursor alcohols, olefins and halides by various methods and functionalizing reagents that include $SOCl_2$ (Tang et al., *J. Chem. Res.*, Synop. 2003, 11, 698), $PBr_3$ (Snow et al., *Synthesis* 2003, 4, 509), ClBr (Movsumzade et al., *Otkrytiya Izobret., Prom. Obraztsy. Tovarnye Znaki* 1974, 51, 68; Movsumzade et al., U.S.S.R. Patent 419503, 1974; *Chem. Abstr.* 1974, 80, 145413), NaI (Kulstad et al., *Tetrahedron Lett.* 1980, 21, 643; Gatto et al., *J. Org. Chem.* 1986, 51, 5373; Tsiakopoulos et al., *ARKIVOC* 2002, 13, 79), and KSCN (Askerov, *Azerbaidzhanskii Khimicheski Zhurnal* 1974, 5-6, 102; Earth Chemical Co., Ltd, Jpn. Kokai Tokkyo Koho 79-171873, 1981). These compounds can have utility as reagents in classical crown ether chemistry (Pederson, *J. Am. Chem. Soc.* 1967, 89, 7017). These compounds can also be useful reagents for the preparation of bioadhesion resistant surface treatments (Kingshott et al., *J. Curr. Opin. Solid State Mater. Sci.* 1999, 4, 403), for the pendant functionalization of rigid rod macromolecules into processable molecular composites (Lauter et al., *Macromolecules* 1997, 30, 2092), and for transforming large dye chromophores into intrinsic liquids (Snow et al., *J. Porphyrins Phthalocyanines* 2000, 4, 518). Recent interest in both water-soluble gold nanoclusters stabilized by ligands containing short ethylene oxide oligomers (Foos et al., *Chem. Mater.* 2002, 14, 2401; Clark et al., *Synthesis* 2006, 7, 1083; Foos et al., *Langmuir* 2004, 20, 10657) and difunctional solubilizing tether agents for monomer/polymer synthesis via Williamson coupling (Allan et al., *J. Org. Chem.* 1994, 59, 7695) required analysis of convenient routes towards several related compounds.

BRIEF SUMMARY

Disclosed herein is a method comprising reacting a toluenesulfonyl-terminated polyoxyethylene compound having the formula $CH_3$—$C_6H_4$—$SO_2$—$(O$—$CH_2$—$CH_2)_n$—$O$—$R^1$ with an ammonium salt having the formula $NR^2_4X$ to form a compound having the formula X—$CH_2$—$CH_2$—$(O$—$CH_2$—$CH_2)_{n-1}$—$R^3$. The value n is a positive integer. X is a halogen, cyanide, cyanate, thiocyanate, or azide. $R^1$ is a terminating group. Each $R^2$ is hydrogen or an alkyl group. —$R^3$ is —O—$R^1$ or —X.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

The disclosed method is a general procedure for the preparation of α,ω-halogen and pseudohalogen terminated oxyethylene oligomers and monodisperse compounds. Polyoxyethylene is also known as polyethylene glycol (PEG) and polyethylene oxide (PEO), and may be an oligomer or polymer. Hydroxyl terminated monodisperse oxyethylene chain compounds and poly(ethylene glycol) oligomers may be readily tosylated and serve as reagents for this method. Substitution may be accomplished upon, for example, stirring for 3-16 hours a solution of a tosyl-protected oxyethylene-oligomer in a polar solvent in the presence of a molar equivalent of ammonium salt. The reaction may proceed in moderate to high yields (>50%) at elevated temperatures (>65° C.) and under an oxygen free atmosphere. These compounds and oligomers may be used as intermediates in the syntheses of surface modifying agents, of corrosion and absorption resistant coatings, and in other polymer synthesis. The method can also position identical or different halogens at the α- and ω-positions of the oxyethylene chain.

Disclosed herein is a method of nucleophilically or otherwise substituting a p-toluene sulfonate group (tosyl) terminating a polyoxyethylene chain with another chemical group. Eq. 1 shows examples using a ditosyl and a monotosyl PEO. The chemical group may be any group that can form an anion in an ammonium salt. The method uses a PEO (also known as polyethylene glycol) having at least one tosyl group at the end. If there is only one tosyl group, the other end of the PEO chain may have any other terminating group, including, but not limited to, organic groups, hydrocarbons, alkyl groups, and halo-substitutes thereof The PEO chain may be a monomer, oligomer, or polymer having any number of repeat units (n), including but not limited to, n=1, 2, 3, 4, 5, 6, 7, 8, 9, and 10 or more. In a monodisperse PEO, n may be, for example 2 to 10. In a polydisperse PEO, meaning a mixture of PEOs of different molecular weights, n may have an average value of, for example, 2 to 50.

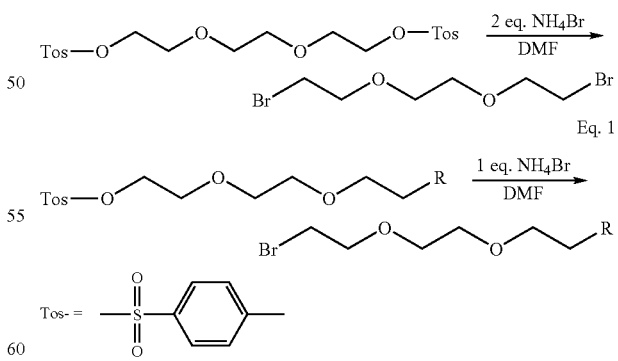

Eq. 1

The tosylate compounds may be made, for example, by reacting the corresponding alcohol with tosyl chloride in a pyridine-dichloromethane mixture as in Eq. 2 (Selve et al., *Tetrahedron*, 1991, 47, 411; Christensen et al., *Synthesis*, 2000, 12, 1695; Snow et al., *Synthesis*, 2003, 4, 509-512).

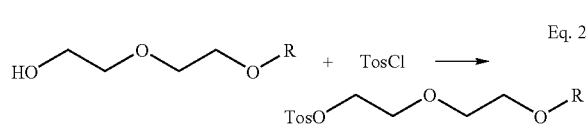

Eq. 2

The ammonium salt may include $NH_4^+$, or any or all of the hydrogen atoms may be substituted by alkyl groups, such as n-butyl. Suitable groups for the anion in the salt include, but are not limited to, fluoride, chloride, bromide, iodide, and the pseudo halogens cyanide, cyanate, thiocyanate, and azide.

Some simple ammonium salts of the general type $NH_4X$ may be commercially abundant, relatively inexpensive, and easily removed following aqueous workup of the reaction mixture. Although the ammonium salts used were not soluble in tetrahydrofuran compared to their alkylammonium analogues, they were soluble in polar organic solvents such as dimethyl sulfoxide and N,N-dimethyl formamide. These solvents were particularly useful since they did not require the rigorous drying and purification procedures typical for tetrahydrofuran and for their generally broad solubility. Other polar, aprotic, organic solvents may also be used. Limited kinetic studies were formerly reported using dipolar aprotic solvent hexamethylphosphoric triamide, for nucleophilic substitution between ethyl tosylate and chloride and bromide ions (Müller et al., *Helv. Chim. Acta*, 1972, 55, 2965).

There may be two advantages in the preparation of the tosylate intermediate: (1) this route appears to avoid side reactions that generate inseparable byproducts previously observed (Snow et al., *Synthesis*, 2003, 4, 509) and (2) as a result of solubility differences, mono-tosylated intermediates are separable from oligo ethylene glycol reactant and disubstituted tosylated byproduct. This distinction may be particularly important for the preparation of unsymmetrically terminated oxyethylene chain molecules.

Experiments reveal that the substituted products may be obtained without significant isolation/purification difficulties caused by side product formation. Since glycols, ammonium salts, modified ethoxy-ethanols and the tosyl chloride used to convert the glycolic alcohols to tosylated end groups are relatively cheap, commercially available and abundant, the method may be practical in large, scalable quantities as well as useful for synthesizing previously difficult difunctional intermediates.

The products may be useful for surface treatments for protection against corrosion and non-specific adsorption, nano-electronics, solubilizing pigments and rigid rod polymers, and chemical sensing. Other uses include intermediates to be used in the preparation of emulsion stabilization agents, aqueous solubilizing agents and in biocompatibilization of synthetic surfaces. The compounds may also self-assemble onto gold nanoclusters.

The following examples are given to illustrate specific applications. These specific examples are not intended to limit the scope of the disclosure in this application.

Examples 1-12

Initially, a commercial glycol and two modified ethoxy-ethanols, tri(ethylene glycol), 2-(2-methoxyethoxy)ethanol and 2-[2-(2-chloroethoxy)-ethoxy]ethanol, were chosen for further experimentation. Tri(ethylene glycol), 2-(2-methoxyethoxy)ethanol, 2-[2-(2-chloroethoxy)-ethoxy]ethanol, p-toluenesulfonyl chloride, ammonium bromide, iodide, thiocyanate and fluoride, diethyl ether and dimethyl sulfoxide were commercially available from Aldrich and used as received. Acetone, N,N-dimethyl formamide, pyridine, dichloromethane and methanol were commercially available from Fisher and used as received. Ammonium chloride was commercially available from Malinckrodt and used as received. Tetra(ethylene glycol) was commercially available from Fluka and used as received. The alcohols were converted to their respective tosylates by reaction with tosyl chloride in a pyridine-dichloromethane mixture in moderate yield (Selve et al., *Tetrahedron*, 1991, 47, 411; Christensen et al., *Synthesis*, 2000, 12, 1695).

Ammonium chloride, bromide, iodide and thiocyanate salts were selected as nucleophilic reagents for reaction with three model tosylates (see Table 1). It was determined by solubility tests that ammonium iodide was more suitable in N,N-dimethyl formamide, whereas chloride, bromide and thiocyanate dissolved readily in dimethyl sulfoxide. It was also noted that reaction temperatures greater than 65° C. were required for complete conversion of the tosylate to the halide or thiocyanate for samples stirring for a minimum of 4 h. Selective conversion reactions were typically heated to 70° C. overnight, whereas non-competitive reactions were performed at slightly elevated temperatures of 80-85° C. for 4-5 h.

TABLE 1

| Example # | R | X | R' | Conditions | Yield (%) |
|---|---|---|---|---|---|
| 1 | —$C_2H_4$—OTos | Cl | —$C_2H_4$—Cl | 4 eq., DMSO 85° C., 5 hrs | 71 |
| 2 | —$C_2H_4$—Cl | Cl | —$C_2H_4$—Cl | 1.2 eq., DMSO 70° C., 16 hrs | 64 |
| 3 | —$CH_3$ | Cl | —$CH_3$ | 2 eq., DMSO 80° C., 5 hrs | 51 |
| 4 | —$C_2H_4$—OTos | SCN | —$C_2H_4$—SCN | 4 eq., DMSO 80° C., 5 hrs | 86 |
| 5 | —$C_2H_4$—Cl | SCN | —$C_2H_4$—Cl | 1.2 eq., DMSO 75° C., 16 hrs | 71 |
| 6 | —$CH_3$ | SCN | —$CH_3$ | 2 eq., DMSO 80° C., 5 hrs | 83 |
| 7 | —$C_2H_4$—OTos | I | —$C_2H_4$—I | 4 eq., DMF 80° C., 5 hrs | 85 |

TABLE 1-continued

TosO−CH₂CH₂−O−CH₂CH₂−O−R  $\xrightarrow{NH_4X}$  X−CH₂CH₂−O−CH₂CH₂−O−R'

| Example # | R | X | R' | Conditions | Yield (%) |
|---|---|---|---|---|---|
| 8 | —C$_2$H$_4$—Cl | I | —C$_2$H$_4$—Cl | 1.2 eq., DMF 70° C., 16 hrs | 70 |
| 9 | —CH$_3$ | I | —CH$_3$ | 2 eq., DMF 80° C., 4 hrs | 76 |
| 10 | —C$_2$H$_4$—OTos | Br | —C$_2$H$_4$—Br | 4 eq., DMSO/DMF, 85° C., 5 hrs | 52, 76 |
| 11 | —C$_2$H$_4$—Cl | Br | —C$_2$H$_4$—Cl | 1.2 eq., DMSO 70° C., 16 hrs | 53 |
| 12 | —CH$_3$ | Br | —CH$_3$ | 2 eq., DMSO 85° C., 4 hrs | 63 |

All synthetic procedures were performed under an inert nitrogen atmosphere with oven-dried glassware. $^1$H and $^{13}$C NMR were recorded on a Bruker Avance-300 instrument. Chemical shifts were referenced to the residual chloroform peak at 7.26 and 77.0 ppm, respectively. Proton and carbon NMR spectra of reacted species were compared to published material and analyzed for side products, conversion and yields.

Representative experimental procedure for the synthesis of 1,8-diiodo-3,6-dioxaoctane 7: Under an atmosphere of nitrogen, N,N-dimethyl formamide (5 mL) was added to tri(ethylene glycol)di(p-toluenesulfonate) (0.20 g, 0.44 mmol) and ammonium iodide (0.65 g, 1.7 mmol). After stirring for 5 h at 80° C., the reaction mixture was poured directly into a separatory funnel containing distilled water (20 mL) and diethyl ether (20 mL). The aqueous phase was extracted with diethyl ether (2×20 mL) and the organic layers were combined, washed with distilled water (2×20 mL), dried with MgSO$_4$, filtered, passed through an activated plug of alumina (Bodman Neutral-Super I) and concentrated in vacuo to reveal an analytically pure product.

Yields greater than 50% were obtained under these conditions for experiments 1-12 (Table 1). Selective conversion for samples 5, 8 and 11 were achieved using 1.2 M equiv of ammonium salt at 70-75° C. for 16 h. It was discovered that a slight ammonium reagent excess did not produce a mixture of products by competitive reaction with the chlorine, although higher molar equivalencies (>1.3) revealed mono- and disubstituted products. These results were particularly advantageous for further chemoselective reactions. For non-competitive experiments 1-4, 6, 7, 9, 10 and 12, an excess of ammonium reagent was utilized for efficient conversion and shorter reaction times. For 10a and 10b, appropriate choice of solvent improved yields from 52% with DMSO to 76% with DMF.

Attempts to employ more common solvents in place of the aprotic solvents were not successful. Methanol and acetone were investigated, but starting material was recovered for each attempt. Generally, poor solubility of the tosylated reactant in methanol and poor solubility of the ammonium salt in acetone were attributing factors.

Attempts to employ ammonium fluoride as a reagent for reaction with the three tosylated compounds in dimethyl sulfoxide, N,N-dimethyl formamide and methanol were unsuccessful. Despite varying conditions and workup, neither product nor starting material was ever recovered. Substitution of fluoride for a tosyl group at the end of an alkane chain has been reported using tetrabutylammonium fluoride in tetrahydrofuran at room temperature (Nagatsugi et al., *J. Fluorine Chem.* 1992, 56, 373). These conditions have also been successful on a tosylate terminated oxyethylene chain.

Yields were generally equivalent or superior to alternate published procedures. For instance, experiment 8 reveals more than double the yield found from the conversion of 1,8-dichloro-3,6-dioxaoctane and sodium iodide in refluxing acetone and an identical yield for experiment 7 under similar conditions (Kulstad et al., *Tetrahedron Lett.*, 1980, 21, 643). The liquids possessed similar physical properties identical with those reported.

Tetra(ethylene glycol)di(p-toluenesulfonate) (Karakaplan et al., *Tetrahedron. Asymmetry*, 2005, 16, 2119) underwent nucleophilic substitution with ammonium iodide in N,N-dimethyl formamide at 80° C. for 5 h to form 1,11-diiodo-3,6,9-trioxaundecane. Compared to the previously reported 4 day conversion required from 1,11-dichloro-3,6,9-trioxaundecane with sodium iodide/acetone in 67% yield (Jousselme et al., *J. Am. Chem. Soc.*, 2003, 125, 136), results were encouraging. The method required a short reaction time for complete conversion and resulted in a higher yield. The diiodide product represented in Eq. 3 is one oxyethylene unit longer than the product in Table 1, entry 7. The isolated yield decreased from 85% to 75% as a result of this one unit extension in chain length. This lower yield may a consequence of purification difficulty due to increasing chain length rather than terminal group reactivity differences.

Example 13

1-Fluoro-3,6-dioxooctan-1-ol

First, 8-tosyloxy-3,6-dioxooctan-1-ol was prepared by a slight modification of the procedure of Kuijpers (Kuijpers et al., *Tetrahedron* 1993, 49, 10931). Briefly, p-toluenesulfonyl chloride (7.50 g, 40.0 mmol) was added to a solution of triethylene glycol (60.0 g, 40.0 mmol) in pyridine (6.5 mL) and dichloromethane (400 mL) and under nitrogen. After stirring for 18 hr at room temperature, the solvent was concentrated under reduced pressure. The residue was dissolved in ethyl acetate (200 mL) and washed with aq. NaCl solution (3×200 mL). The aq. extract was back extracted with ethyl acetate (2×100 mL), and the combined ethyl acetate phases were dried over MgSO$_4$. After filtering and evaporating to dryness the product was purified on a silica column to yield a clear oil (9.30 g, 75%). $^1$H NMR (300 MHz, CDCl$_3$, TMS): δ 7.82 (d, $^3J_{HH}$=8.1 Hz, 2H), 7.36 (d, $^3J_{HH}$=8.1 Hz, 2H), 7.19 (t, $^3J_{HH}$=3.6 Hz, 2H), 3.59-3.78 (m, 10H), 2.47 (s, 3H). $^{13}$C NMR (75 MHz, CDCl$_3$, TMS): δ 144.86, 132.93, 129.82, 127.96, 72.48, 70.77, 70.34, 69.13, 68.70, 61.74, 21.62. IR (NaCl): ν=3421, 2886, 1594, 1358, 1169, 664 cm$^{-1}$.

The final product was made from the 8-tosyloxy-3,6-dioxooctan-1-ol. A 3-neck 100 mL reaction flask was fitted with a dropping funnel, thermometer, stirring bar and nitrogen inlet and purged with dry nitrogen. The triethylene glycol monotosylate, 5, (10.016 g, 32.9 mmol) was weighed into the reaction flask followed by pipette addition of dry THF (31.0 mL). After dissolution, tetrabutyl ammonium fluoride (37.0 mL 1.0 M/THF, 37.0 mmol) was transferred to the dropping funnel and added dropwise to the stirred reaction mixture. The reaction was stirred at 22° C. for 11 hr under N$_2$ and developed a dark brown coloration. The reaction was worked up by rotary evaporator concentration (5° C./20 mm) to remove THF then vacuum distilled (105-115° C./5 mm) to collect 3.58 g of an amber liquid. This crude product was redistilled (114-116° C./4 mm) to yield 3.327 g (67% yield) of product as a colorless liquid. $^1$H NMR (300 MHz, CDCl$_3$, TMS): δ=2.95 (s, 1H), 3.5-3.8 (m, 10H), 4.52 (d $^2J_{HF}$=51 Hz of t $^3J_{HH}$=4 Hz, 2H). $^{13}$C NMR (75 MHz, CDCl$_3$, TMS): δ=61.54, 70.19, 70.38, 70.66, 72.45, 82.95. $^{19}$F NMR (282 MHz, CDCl$_3$, CFCl$_3$): δ=−223.33 (t $^2J_{HF}$=48 Hz of t $^3J_{HH}$=31 Hz). IR (NaCl): ν=3450, 2885, 1358, 1014 cm$^{-1}$. CI MS: m/z 153 (MH$^+$).

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A method comprising:
reacting a toluenesulfonyl-terminated polyoxyethylene compound having the formula:

CH$_3$—C$_6$H$_4$—SO$_2$—(O—CH$_2$—CH$_2$)$_n$—O—R$^1$;

with an ammonium salt having the formula:

NH$_4$X to form a compound having the formula:

X—CH$_2$—CH$_2$—(O—CH$_2$—CH$_2$)$_{n-1}$—R$^3$;

wherein n is a positive integer;
wherein X is chloride, bromide, iodide, cyanide, cyanate, thiocyanate, or azide;
wherein R$^1$ is hydrogen, a hydrocarbon, halo-substituted hydrocarbon, or CH$_3$—C$_6$H$_4$—SO$_2$—and
wherein —R$^3$ is —O—R$^1$ when R$^1$ is hydrogen or a hydrocarbon, halo-substituted hydrocarbon thereof or —X when R$^1$ is CH$_3$—C$_6$H$_4$—SO$_2$—.

2. The method of claim 1;
wherein the toluenesulfonyl-terminated polyoxyethylene compound is monodisperse; and
wherein n is from 2 to 10.

3. The method of claim 1;
wherein the toluenesulfonyl-terminated polyoxyethylene compound is polydisperse; and
wherein the average value of n is from 2 to 50.

4. The method of claim 1, wherein R$^1$ is CH$_3$—C$_6$H$_4$—SO$_2$—.

5. The method of claim 1, wherein R$^1$ is Cl—CH$_2$—CH$_2$— or CH$_3$—.

6. The method of claim 1, wherein R$^1$ is H—.

7. The method of claim 1;
wherein the toluenesulfonyl-terminated polyoxyethylene compound is:

CH$_3$—C$_6$H$_4$—SO$_2$—(O—CH$_2$—CH$_2$)$_n$—O—SO$_2$—C$_6$H$_4$—CH$_3$; and wherein the compound is:

X—CH$_2$—CH$_2$—(O—CH$_2$—CH$_2$)$_{n-1}$—X.

8. The method of claim 1, wherein the reaction is performed in a polar, aprotic, organic solvent.

9. The method of claim 7, wherein the solvent is dimethyl sulfoxide, N,N-dimethylformamide, or tetrahydrofuran.

* * * * *